US012685499B2

(12) United States Patent

Tsuyuki

(10) Patent No.: US 12,685,499 B2
(45) Date of Patent: Jul. 21, 2026

(54) PHOTON COUNTING CT APPARATUS AND IMAGING METHOD

(71) Applicant: Canon Kabushiki Kaisha, Tokyo (JP)

(72) Inventor: Masaharu Tsuyuki, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 50 days.

(21) Appl. No.: 18/448,201

(22) Filed: Aug. 11, 2023

(65) Prior Publication Data

US 2024/0065655 A1       Feb. 29, 2024

(30) Foreign Application Priority Data

Aug. 25, 2022    (JP) ................................. 2022-134217

(51) Int. Cl.
| | |
|---|---|
| *A61B 6/00* | (2024.01) |
| *A61B 6/03* | (2006.01) |
| *A61B 6/42* | (2024.01) |
| *A61B 6/46* | (2024.01) |

(52) U.S. Cl.
CPC ............ *A61B 6/4241* (2013.01); *A61B 6/032* (2013.01); *A61B 6/463* (2013.01); *A61B 6/481* (2013.01)

(58) Field of Classification Search
CPC ....... A61B 6/4241; A61B 6/032; A61B 6/463; A61B 6/481; A61B 6/027; A61B 6/4035; A61B 6/467; A61B 6/486; A61B 6/5205
See application file for complete search history.

(56) References Cited

U.S. PATENT DOCUMENTS

| | | | | |
|---|---|---|---|---|
| 2016/0058404 A1* | 3/2016 | Nitta | .................... | A61B 6/4241 |
| | | | | 382/131 |
| 2016/0113609 A1* | 4/2016 | Tsuyuki | ................. | A61B 6/482 |
| | | | | 600/425 |
| 2021/0259654 A1* | 8/2021 | Yao | ........................ | A61B 6/469 |

FOREIGN PATENT DOCUMENTS

JP          2015-33578 A       2/2015

* cited by examiner

*Primary Examiner* — Kaitlyn E Sebastian
(74) *Attorney, Agent, or Firm* — Oblon, McClelland, Maier & Neustadt, L.L.P.

(57) ABSTRACT

A photon counting CT apparatus of an embodiment includes processing circuitry. The processing circuitry is configured to generate data from which a plurality of types of contrast-enhancing substances can be discriminated on the basis of detection results obtained by monitoring scanning performed on a subject into which the plurality of types of contrast-enhancing substances have been injected.

5 Claims, 6 Drawing Sheets

<u>C2</u>

| FIRST CONTRAST AGENT | |
| --- | --- |
| CONDITION NUMBER | DETERMINATION CONDITIONS |
| 1 | A HAS BEEN EXCEEDED |
| 2 | HAVE BECOME B OR LESS SINCE A WAS EXCEEDED |
| 3 | CONTINUE B OR LESS FOR X SECONDS OR LONGER SINCE A WAS EXCEEDED |
| 4 | CONTINUE [B, C] FOR X SECONDS OR LONGER SINCE A WAS EXCEEDED |
| 5 | Y SECONDS HAVE ELAPSED SINCE PEAK WAS EXCEEDED |

FOR EACH CONTRAST AGENT

PHOTON COUNTING CT APPARATUS AND IMAGING METHOD

CROSS-REFERENCE TO RELATED APPLICATION

The present application claims priority based on Japanese Patent Application No. 2022-134217 filed Aug. 25, 2022, the content of which is incorporated herein by reference.

FIELD

Embodiments disclosed in this specification and drawings relate to a photon counting CT apparatus and an imaging method.

BACKGROUND

In imaging with an X-ray computed tomography (CT) apparatus, a method of injecting a contrast agent into a subject and observing changes in time series in a specific site (for example, a tumor or the like) of the subject set as a region of interest (ROI) is used. In imaging using a contrast agent, it is necessary to start scanning at a timing when the contrast agent reaches a region of interest. Real Prep. is known as a technique for optimally controlling such scanning timing. In Real Prep., changes due to a contrast agent are monitored while monitoring scanning is performed, and when predetermined conditions are met, main scanning is automatically started.

There are cases in which a plurality of types of contrast agents are used depending on an examination purpose. In such cases, it is necessary to start scanning at timings when a plurality of types of contrast agents injected at different timings or at the same time have reached regions of interest determined for the respective contrast agents. However, in the conventional Real Prep., it is impossible to control an optimal scan timing because it is impossible to distinguish between a plurality of types of contrast agents. Moreover, in these cases, since it is necessary to perform imaging individually (at different timings) for each contrast agent, it takes time and effort to align a subject.

DETAILED DESCRIPTION

An X-ray CT apparatus and an imaging method of an embodiment will be described below with reference to the drawings. The X-ray CT apparatus of the embodiment is a photon counting computed tomography (CT) apparatus. A photon counting CT apparatus discriminates an inspection target substance through which X-rays have passed using a direct detector such as a semiconductor detector with excellent energy resolution. For example, in imaging using a plurality of types of contrast-enhancing substances, it is possible to discriminate between a plurality of types of contrast-enhancing substances in a subject.

The photon counting CT apparatus of the embodiment include includes processing circuitry. The processing circuitry is configured to generate data from which a plurality of contrast-enhancing substances can be discriminated on the basis of detection results obtained by monitoring scanning performed on a subject into which the plurality of contrast-enhancing substances have been injected.

A contrast-enhancing substance is a substance that enables generation of an image enhanced by adding contrast to specific tissues when imaging is performed in a state in which the contrast-enhancing substance has been injected into a subject. Contrast-enhancing substances are, for example, contrast agents. Contrast agents include, for example, an iodine contrast agent, a gadolinium contrast agent, and the like. Alternatively, contrast-enhancing substances are, for example, Xe which is a gas used for cerebral blood flow examination, Sonazoid (registered trademark) (Perflubutane) which is a gas used for ultrasonic examination, and other therapeutic medicines, nutrient solutions, physiological saline solutions, and the like injected into the body of a subject.

The contrast effect is represented by a specific index value determined for each substance. A high contrast effect indicates that an image in which specific tissues are emphasized by, for example, contrasting is easily generated. A low contrast effect indicates that it is difficult to generate an image in which specific tissues are emphasized by, for example, contrasting. For example, in the case of a contrast agent, a high contrast effect means a high degree of attenuation of X-rays (a high degree of absorption of X-rays) in an X-ray CT apparatus, and a low contrast effect means a low degree of attenuation of X-rays (a low degree of absorption of X-rays) in an X-ray CT apparatus. In this case, the contrast effect is represented by an index value based on an X-ray absorption amount. In the following, as a contrast-enhancing substance, a "contrast agent" will be described as a contrast-enhancing substance.

Embodiment

[Configuration of X-Ray CT Apparatus]

Figure 1:
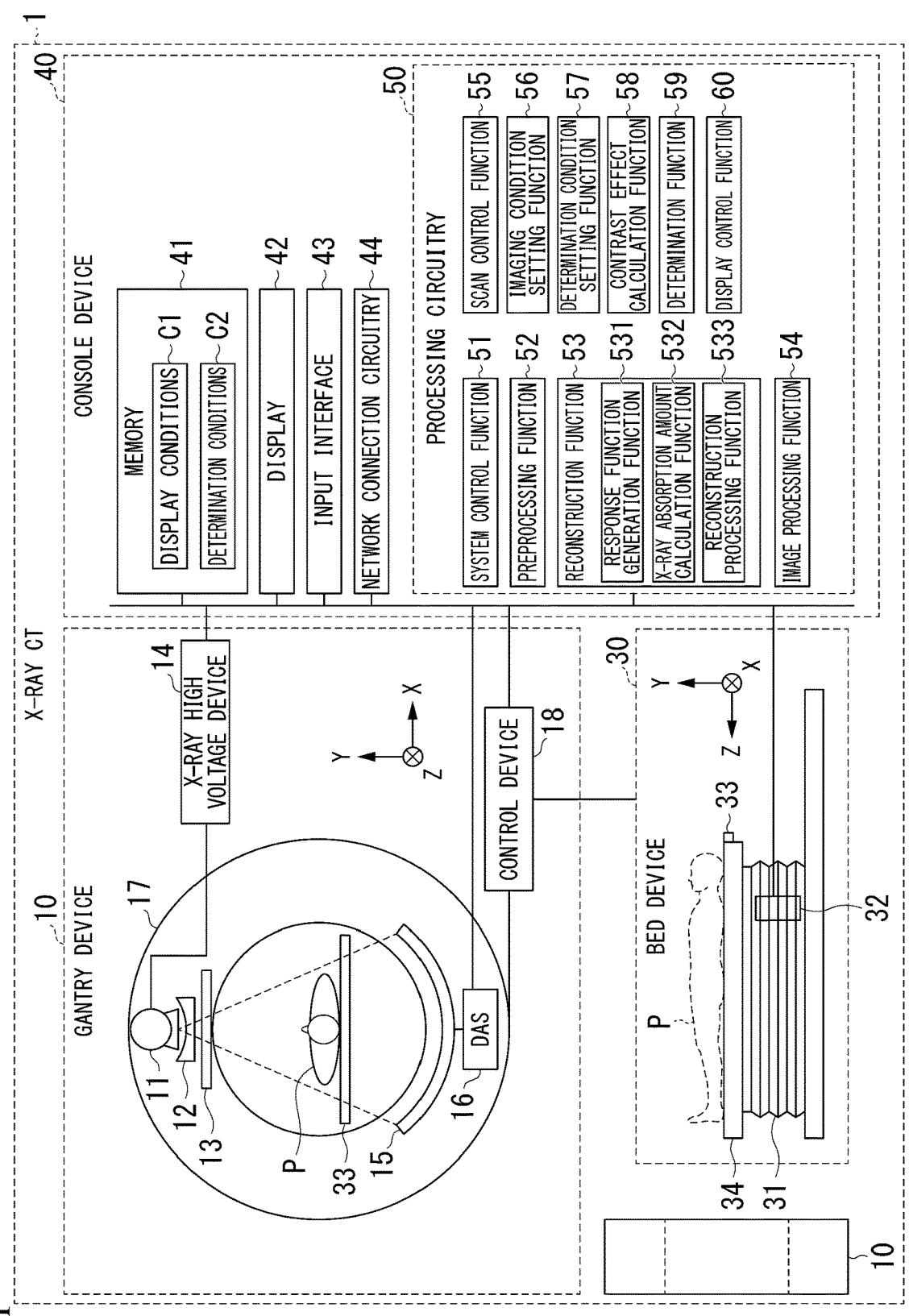
FIG. 1 is a diagram showing an example of an X-ray CT apparatus 1 according to an embodiment.

FIG. 1 is a diagram showing an example of an X-ray CT apparatus 1 according to an embodiment. The X-ray CT apparatus 1 includes, for example, a gantry device 10, a bed device 30, and a console device 40. Although FIG. 1 shows both a diagram of the gantry device 10 viewed in the Z-axis direction and a diagram of the gantry device 10 viewed in the X-axis direction for convenience of description, there is in fact one gantry device 10. In the present embodiment, the rotation axis of a rotating frame 17 in a non-tilt state or the longitudinal direction of a top plate 33 of the bed device 30 is defined as the Z-axis direction, an axis orthogonal to the Z-axis direction and parallel to the floor surface is defined as the X-axis direction, and a direction perpendicular to the Z-axis direction and perpendicular to the floor surface is defined as the Y-axis direction.

The gantry device 10 includes, for example, an X-ray tube 11, a wedge 12, a collimator 13, an X-ray high voltage device 14, an X-ray detector 15, a data acquisition system (hereinafter DAS) 16, the rotating frame 17, and a control device 18.

The X-ray tube 11 generates X-rays by radiating thermal electrons from a cathode (filament) to an anode (target) when a high voltage is applied thereto from the X-ray high voltage device 14. The X-ray tube 11 includes a vacuum tube. For example, the X-ray tube 11 is a rotating anode type X-ray tube that generates X-rays by radiating thermal electrons to a rotating anode.

The wedge 12 is a filter for adjusting a dose of X-rays radiated from the X-ray tube 11 to a subject P. The wedge 12 attenuates X-rays passing through the wedge 12 such that a distribution of the dose of X-rays radiated from the X-ray tube 11 to the subject P becomes a predetermined distribution. The wedge 12 is also called a wedge filter or a bow-tie filter. The wedge 12 is obtained by, for example, processing aluminum such that it has a predetermined target angle and a predetermined thickness.

The collimator 13 is a mechanism for narrowing down a radiation range of X-rays that have passed through the wedge 12. The collimator 13 narrows down the radiation range of X-rays by, for example, forming a slit by combining a plurality of lead plates. The collimator 13 may also be called an X-ray diaphragm. A narrowing range of the collimator 13 may be mechanically drivable.

The X-ray high voltage device 14 includes, for example, a high voltage generation device which is not shown and an X-ray control device which is not shown. The high voltage generation device has electric circuitry including a transformer, a rectifier, and the like and generates a high voltage to be applied to the X-ray tube 11. The X-ray control device controls the output voltage of the high voltage generation device in accordance with an amount of X-rays to be generated by the X-ray tube 11. The high voltage generation device may boost a voltage using the transformer described above or may boost the voltage using an inverter. The X-ray high voltage device 14 may be provided on the rotating frame 17 or may be provided on the side of a fixed frame (not shown) of the gantry device 10.

The X-ray detector 15 detects the intensity of X-rays generated by the X-ray tube 11 and incident through the subject P. The X-ray detector 15 outputs an electrical signal (which may be an optical signal or the like) corresponding to the detected intensity of X-rays to the DAS 16. The X-ray detector 15 has, for example, a plurality of X-ray detection element arrays. Each of the plurality of X-ray detection element arrays has a plurality of X-ray detection elements arranged in a channel direction along an arc having the focal point of the X-ray tube 11 as a center. The plurality of X-ray detection element arrays are arranged in a slice direction (column direction or row direction).

The X-ray detector 15 is, for example, a direct detection type detector. As the X-ray detector 15, for example, a semiconductor diode having electrodes attached to both ends of a semiconductor can be applied. X-ray photons incident on the semiconductor are converted into electron-hole pairs. The number of electron-hole pairs generated by incidence of one X-ray photon depends on the energy of the incident X-ray photon. Electrons and holes are each attracted to a pair of electrodes formed at both ends of the semiconductor. A pair of electrodes generates an electric pulse having a crest value corresponding to the charge of electron-hole pairs. A single electric pulse has a crest value corresponding to the energy of an incident X-ray photon.

The DAS 16 acquires count data indicating a count number of X-ray photons detected by the X-ray detector 15 for a plurality of energy bins, for example, according to a control signal from the control device 18. The count data for the plurality of energy bins corresponds to an energy spectrum with respect to X-rays incident on the X-ray detector 15 modified in accordance with the response characteristics of the X-ray detector 15. The DAS 16 outputs detection data based on digital signals to the console device 40. Detection data is a digital value of count data identified by a channel number and a row number of an X-ray detection element that is a generation source, and a view number indicating an acquired view. A view number is a number that changes according to rotation of the rotating frame 17 and is a number that is incremented according to rotation of the rotating frame 17, for example. Therefore, the view number is information indicating a rotation angle of the X-ray tube 11. A view period is a period that falls between a rotation angle corresponding to a certain view number and a rotation angle corresponding to the next view number.

The DAS 16 may detect switching of a view from a timing signal input from the control device 18, from an internal timer, or from a signal obtained from a sensor which is not shown. In a case where X-rays are continuously emitted from the X-ray tube 11 during full scanning, the DAS 16 acquires detection data groups for the entire circumference (for 360 degrees). In a case where X-rays are continuously emitted from the X-ray tube 11 during half scanning, the DAS 16 acquires detection data for a half circumference (for 180 degrees).

Figure 2:
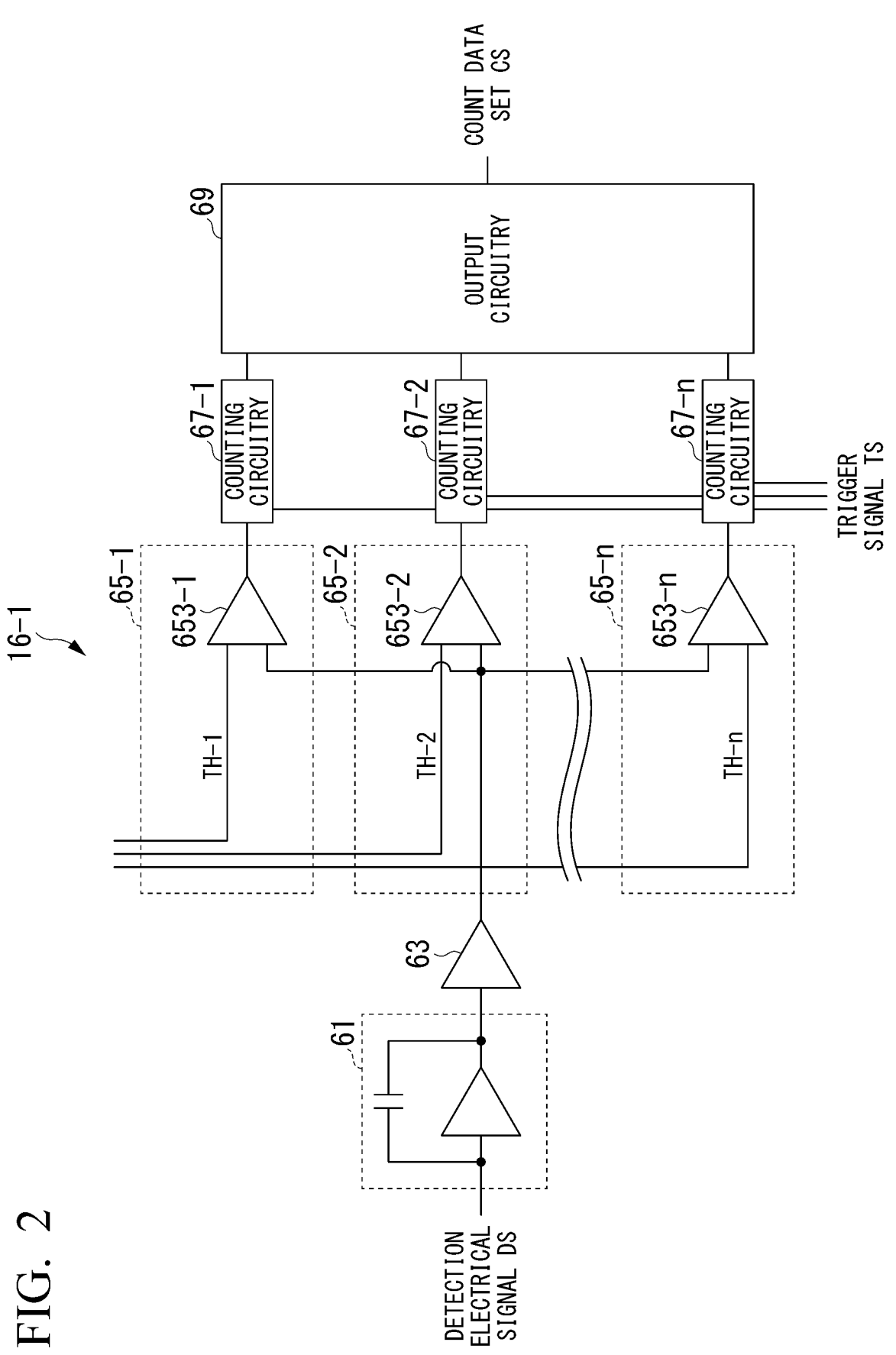
FIG. 2 is a diagram showing an example of a configuration of a data acquisition system (DAS) 16 according to an embodiment.

FIG. 2 is a diagram showing an example of a configuration of the DAS 16 according to the embodiment. The DAS 16 includes as many readout channels as the number of channels corresponding to the number of X-ray detection elements. These read channels are implemented in parallel in an integrated circuit, such as an application specific integrated circuit (ASIC). FIG. 2 shows only a configuration of a DAS 16-1 for one read channel.

The DAS 16-1 includes preamplifier circuitry 61, waveform shaping circuitry 63, a plurality of wave height discrimination circuitry 65, a plurality of counter circuitry 67, and output circuitry 69. The preamplifier circuitry 61 amplifies a detection electrical signal DS (current signal) from an X-ray detection element to which it is connected. For example, the preamplifier circuitry 61 converts the current signal from the X-ray detection element to which it is connected into a voltage signal having a voltage value (wave height value) proportional to the charge amount of the current signal. The waveform shaping circuitry 63 is connected to the preamplifier circuitry 61. The waveform shaping circuitry 63 shapes the waveform of the voltage signal from the preamplifier circuitry 61. For example, the waveform shaping circuitry 63 reduces the pulse width of the voltage signal from the preamplifier circuitry 61.

A plurality of counting channels corresponding to the number of energy bands (energy bins) are connected to the waveform shaping circuitry 63. In a case where n energy bins are set, n counting channels are provided in the waveform shaping circuitry 63. Each counting channel has wave height discrimination circuitry 65-$n$ and counting circuitry 67-$n$.

Each of the wave height discrimination circuitry 65-$n$ discriminates the energy of X-ray photons detected by the X-ray detection element, which is the wave height value of the voltage signal from the waveform shaping circuitry 63. For example, the wave height discrimination circuitry 65-$n$ has comparison circuitry 653-$n$. A voltage signal from the waveform shaping circuitry 63 is input to one input terminal of each comparison circuitry 653-$n$. A reference signal TH (reference voltage value) corresponding to a different threshold value is supplied from the control device 18 to the other input terminal of each comparison circuitry 653-n.

For example, a reference signal TH-1 is supplied to comparison circuitry 653-1 for an energy bin bin1, a reference signal TH-2 is supplied to comparison circuitry 653-2 for an energy bin bin2, and a reference signal TH-n is supplied to comparison circuitry 653-n for an energy bin binn. Each reference signal TH has an upper limit reference value and a lower limit reference value. Each comparison circuitry 653-n outputs an electrical pulse signal in a case where the voltage signal from the waveform shaping circuitry 63 has a wave height value corresponding to the energy bin corresponding to each reference signal TH. For example, in a case where the wave height value of the voltage signal from the waveform shaping circuitry 63 corresponds to the energy bin bin1 (falls between the reference signals TH-1 and TH-2), the comparison circuitry 653-1 outputs an electrical pulse signal. On the other hand, in a case where the wave height value of the voltage signal from the waveform shaping circuitry 63 does not correspond to the energy bin bin1, the comparison circuitry 653-1 for the energy bin bin1 does not output an electrical pulse signal. Further, in a case where the wave height value of the voltage signal from the waveform shaping circuitry 63 corresponds to the energy bin bin2 (falls between the reference signals TH-2 and TH-3), for example, the comparison circuitry 653-2 outputs an electric pulse signal.

The counting circuitry 67-n counts electrical pulse signals from the wave height discrimination circuitry 65-n at a read cycle that matches a view switching cycle. For example, a trigger signal TS is supplied to the counting circuitry 67-n from the control device 18 at each view switching timing. By being triggered by supply of the trigger signal TS, the counting circuitry 67-n adds 1 to a count number stored in the internal memory each time an electrical pulse signal is input from the wave height discrimination circuitry 65-n. By being triggered by supply of the next trigger signal, the counting circuitry 67-n reads count number data (that is, the count data) stored in the internal memory and supplies the read count number data to the output circuitry 69. Further, the counting circuitry 67-n resets the count number accumulated in the internal memory to an initial value each time the trigger signal TS is supplied. In this manner, the counting circuitry 67-n counts the count number for each view.

The output circuitry 69 is connected to the counting circuitry 67-n for a plurality of readout channels mounted on the X-ray detector 15. The output circuitry 69 integrates count data from the counting circuitry 67-n for the plurality of readout channels for each of the plurality of energy bins to generate count data for the plurality of readout channels for each view. Count data of each energy bin is a set of count number data defined by a channel, a segment (column), and an energy bin. The count data of each energy bin is transmitted to the console device 40 on a view-by-view basis. The count data on a view-by-view basis is called a count data set CS.

The rotating frame 17 is an annular member that supports the X-ray tube 11, the wedge 12, the collimator 13, and the X-ray detector 15 while facing them. The rotating frame 17 is rotatably supported by a fixed frame around the subject P introduced therein. The rotating frame 17 also supports DAS 16. Detection data output by the DAS 16 is transmitted through optical communication from a transmitter having a light emitting diode (LED) provided on the rotating frame 17 to a receiver having a photodiode provided on a non-rotating part (e.g., fixed frame) of the gantry device 10 and forwarded to the console device 40 by the receiver. A method of transmitting the detection data from the rotating frame 17 to the non-rotating part is not limited to the above-described method using optical communication, and any non-contact transmission method may be employed. The rotating frame 17 is not limited to an annular member and may be a member such as an arm as long as it can support and rotate the X-ray tube 11 and the like.

The X-ray CT apparatus 1 is, for example, a rotate/rotate-type X-ray CT apparatus (third generation CT) in which both the X-ray tube 11 and the X-ray detector 15 are supported by the rotating frame 17 and rotate around the subject P, but not limited to thereto and may be a stationary/rotate-type X-ray CT apparatus (fourth generation CT) in which a plurality of X-ray detection elements arranged in an annular shape are fixed to a fixed frame and the X-ray tube 11 rotates around the subject P.

The control device 18 includes, for example, processing circuitry having a processor such as a central processing unit (CPU). The control device 18 receives an input signal from an input interface attached to the console device 40 or the gantry device 10 and controls operations of the gantry device 10, the bed device 30, and the DAS 16. For example, the control device 18 rotates the rotating frame 17 and tilts the gantry device 10. At the time of tilting the gantry device 10, the control device 18 rotates the rotating frame 17 about an axis parallel to the Z-axis direction on the basis of an inclination angle (tilt angle) input to the input interface. The control device 18 ascertains a rotation angle of the rotating frame 17 from the output of a sensor which is not shown, or the like. The control device 18 also controls energy bins (reference signal TH) of the DAS 16. The control device 18 may be provided in the gantry device 10 or may be provided in the console device 40.

The bed device 30 moves the subject P to be scanned placed thereon and enters the inside of the rotating frame 17 of the gantry device 10. The bed device 30 includes, for example, a base 31, a bed driving device 32, a top plate 33, and a support frame 34. The base 31 includes a housing that supports the support frame 34 such that the support frame 34 is movable in the vertical direction (Y-axis direction). The bed driving device 32 includes a motor and an actuator. The bed driving device 32 moves the top plate 33 along the support frame 34 in the longitudinal direction (Z-axis direction) of the top plate 33. The bed driving device 32 also moves the top plate 33 in the vertical direction (Y-axis direction). The top plate 33 is a plate-shaped member on which the subject P is placed.

The bed driving device 32 may move not only the top plate 33 but also the support frame 34 in the longitudinal direction of the top plate 33. Contrary to the above, the gantry device 10 may be movable in the Z-axis direction, and the rotating frame 17 may be controlled to come around the subject P by moving the gantry device 10. Moreover, both the gantry device 10 and the top plate 33 may be configured to be movable. Further, the X-ray CT apparatus 1 may be an apparatus in which the subject P is scanned in a standing or sitting position. In this case, the X-ray CT apparatus 1 has a subject support mechanism in place of the bed device 30, and the gantry device 10 rotates the rotating frame 17 about the axial direction perpendicular to the floor surface.

The console device 40 includes, for example, a memory 41, a display 42, an input interface 43, network connection circuitry 44, and processing circuitry 50. In the embodiment, the console device 40 is described as being separate from the gantry device 10, but the gantry device 10 may include some or all of the components of the console device 40.

The memory 41 is realized by, for example, a semiconductor element such as a random access memory (RAM) or a flash memory, a hard disk, an optical disk, or the like. The memory 41 stores, for example, display conditions C1, determination conditions C2, and the like. The display conditions C1 define display modes (color, pattern, etc.) at the time of imaging each of a plurality of types of contrast agents. The determination conditions C2 define conditions for determining a timing of main scanning at the time of performing imaging using a plurality of types of contrast agents. The memory 41 also stores, for example, detection data, projection data, reconstructed image data, CT image data, information on the subject P, imaging conditions, and the like. The memory 41 stores count data regarding a plurality of energy bins transmitted from the gantry device 10, for example. Such data may be stored in an external memory with which the X-ray CT apparatus 1 can communicate instead of the memory 41 (or in addition to the memory 41). The external memory is controlled by a cloud server, for example, when the cloud server that manages the external memory receives a read/write request.

The display 42 displays various types of information. For example, the display 42 displays a medical image (CT image) generated by the processing circuitry, a graphical user interface (GUI) image for receiving various operations of an operator such as a doctor or an engineer, and the like. The display 42 is, for example, a liquid crystal display, a cathode ray tube (CRT), an organic electroluminescence (EL) display, or the like. The display 42 may be provided on the gantry device 10. The display 42 may be of a desktop type, or may be a display device (for example, a tablet terminal) capable of wireless communication with the main body of the console device 40.

The input interface 43 receives various input operations of the operator and outputs an electrical signal indicating the content of the received input operation to the processing circuitry 50. For example, the input interface 43 receives operations of inputting acquisition conditions at the time of acquiring detection data or projection data, reconstruction conditions at the time of reconstructing a CT image, image processing conditions at the time of generating post-processed images from CT images, the display conditions C1, the determination conditions C2, energy bin setting conditions, and the like. For example, the input interface 43 is realized by a mouse, a keyboard, a touch panel, a drag ball, a switch, a button, a joystick, a camera, an infrared sensor, a microphone, and the like.

The input interface 43 may be provided in the gantry device 10. Further, the input interface 43 may be realized by a display device (for example, a tablet terminal) capable of wireless communication with the main body of the console device 40. In this specification, the input interface is not limited to those having physical operation parts such as a mouse and a keyboard. For example, examples of the input interface include electrical signal processing circuitry that receives an electrical signal corresponding to an input operation from external input equipment provided separately from the device and outputs the electrical signal to the control circuitry.

The network connection circuitry 44 includes, for example, a network card having a printed circuit board, a wireless communication module, or the like. The network connection circuitry 44 implements an information communication protocol in accordance with the form of a network to be connected.

The processing circuitry 50 controls the overall operation of the X-ray CT apparatus 1, the operation of the gantry device 10, and the operation of the bed device 30. The processing circuitry 50 executes, for example, a system control function 51, a preprocessing function 52, a reconstruction function 53, an image processing function 54, a scan control function 55, an imaging condition setting function 56, a determination condition setting function 57, a contrast effect calculation function 58, a determination function 59, a display control function 60, and the like. These components are realized by, for example, a hardware processor (computer) executing a program (software) stored in the memory 41. The hardware processor means, for example, circuitry such as a CPU, a graphics processing unit (GPU), an application specific integrated circuit (ASIC), or a programmable logic device (e.g., a simple programmable logic device (SPLD) or a complex programmable logic device (CPLD), or a field programmable gate array (FPGA).

Instead of storing the program in the memory 41, the program may be directly embedded in the circuit of the hardware processor. In this case, the hardware processor realizes the functions by reading and executing the program embedded in the circuit. The hardware processor is not limited to being configured as a single circuit and may be configured as one hardware processor by combining a plurality of independent circuits to realize each function. Further, a plurality of components may be integrated into one hardware processor to realize each function.

Each component of the console device 40 or the processing circuitry 50 may be distributed and realized by a plurality of pieces of hardware. The processing circuitry 50 may be realized by a processing device capable of communicating with the console device 40 instead of being a component included in the console device 40. The processing device is, for example, a workstation connected to one X-ray CT apparatus or a device (e.g., cloud server) that is connected to a plurality of X-ray CT apparatuses and collectively executes processing equivalent to that of the processing circuitry 50 which will be described below.

The system control function 51 controls various functions of the processing circuitry 50 on the basis of input operations received through the input interface 43. The system control function 51 sets energy bins, for example. The system control function 51 outputs set energy bin setting conditions to the control device 18.

The preprocessing function 52 performs preprocessing such as offset correction processing, inter-channel sensitivity correction processing, and beam hardening correction on detection data output from the DAS 16.

The reconstruction function 53 reconstructs a photon counting CT image of the subject P on the basis of detection data (count data). The reconstruction function 53 includes, for example, a response function generation function 531, an X-ray absorption amount calculation function 532, and a reconstruction processing function 533. The response function generation function 531 generates response function data representing detector response characteristics. For example, the response function generation function 531 measures a response (i.e., detected energy and detected intensity) of a standard detection system to a plurality of monochromatic X-rays having a plurality of incident X-ray energies through predictive calculations, experiments, and combinations of predictive calculations and experiments, and generates a response function on the basis of measured values of the detected energy and the detected intensity. Further, the response function generation function 531 may generate response function data on the basis of actual measurement values acquired in calibration or the like. The response function defines a relationship between a detected energy for each incident x-ray and an output response of the system. For example, the response function defines a relationship between a detected energy and a detected intensity for each incident x-ray. The generated response function data is stored in the memory 41.

The X-ray absorption amount calculation function 532 calculates an X-ray absorption amount with respect to each of a plurality of ground substances on the basis of count data regarding a plurality of energy bins, the energy spectrum of X-rays incident on the subject P, and the response function stored in the memory 41. The X-ray absorption amount calculation function 532 can calculate an X-ray absorption amount having no influence on the response characteristics of the X-ray detector 15 and the DAS 16 by calculating the X-ray absorption amount using the response function on the basis of the count data and the energy spectrum of the X-rays incident on the subject P. Processing of obtaining the X-ray absorption amount for each ground substance in this manner is also called substance discrimination. Any substance such as calcium, calcification, bone, fat, muscle, air, organ, lesion, hard tissue, soft tissue, and contrast agent can be set as a ground substance. The type of ground substance to be calculated may be determined in advance by an operator or the like via the input interface 43. An X-ray absorption amount indicates the amount of X-rays absorbed by a ground substance. For example, an X-ray absorption amount is defined by a combination of an X-ray attenuation coefficient and an X-ray transmission path length.

The reconstruction processing function 533 reconstructs a photon counting CT image representing a spatial distribution of a ground substance to be imaged among a plurality of ground substances on the basis of the X-ray absorption amount for each of the plurality of ground substances calculated by the X-ray absorption amount calculation function 532 and stores the generated CT image data in the memory 41. The ground substance to be imaged may be of one type or of a plurality of types. The type of ground substance to be imaged may be determined by an operator or the like via the input interface 43.

The reconstruction function 53 is an example of a "reconstructor." That is, the reconstruction function 53 generates data from which a plurality of types of contrast-enhancing substances can be discriminated on the basis of detection results obtained by monitoring scanning performed on a subject into which the plurality of types of contrast-enhancing substances have been injected.

The image processing function 54 converts a CT image data into three-dimensional image data or cross-sectional image data of an arbitrary cross section through a known method on the basis of an input operation received through the input interface 43. Conversion to three-dimensional image data may be performed by the preprocessing function 52.

The scan control function 55 controls detection data acquisition processing in the gantry device 10 by instructing the X-ray high voltage device 14, the DAS 16, the control device 18, and the bed driving device 32. The scan control function 55 performs control for monitoring scanning and main scanning which will be described later. Further, the scan control function 55 controls the operation of each unit at the time of imaging for acquiring positioning images and capturing an image used for diagnosis.

The imaging condition setting function 56 sets imaging conditions on the basis of an input operation received through the input interface 43. The imaging condition setting function 56 sets the type of contrast agent used for imaging, a region of interest (arterial phase, venous phase, tissue, etc.) for each contrast agent, the purpose of examination, and the like as imaging conditions.

The determination condition setting function 57 sets determination conditions on the basis of the imaging conditions set by the imaging condition setting function 56. The determination condition setting function 57 stores the set determination conditions in the memory 41. The determination condition setting function 57 may set determination conditions on the basis of an input operation received through the input interface 43. Details of processing of the determination condition setting function 57 will be described later.

The determination condition setting function 57 is an example of a "determination condition setter." The determination condition setting function 57 sets determination conditions for each of a plurality of contrast-enhancing substances.

The contrast effect calculation function 58 calculates the contrast effect for each of a plurality of types of contrast agents. For example, the reconstruction function 53 calculates an X-ray absorption amount for each of a plurality of types of contrast agents (ground substances) as a contrast effect during a monitoring scanning. In this case, the contrast effect calculation function 58 may be included in the X-ray absorption amount calculation function 532 described above.

The contrast effect calculation function 58 is an example of a "contrast effect calculator." The contrast effect calculation function 58 calculates the contrast effect of each of a plurality of types of contrast-enhancing substances on the basis of data from which the plurality of types of contrast-enhancing substances can be discriminated.

The determination function 59 determines whether or not the determination conditions C2 stored in the memory 41 are satisfied. The determination function 59 determines, for example, whether or not determination conditions corresponding to a combination of determination conditions set for each contrast agent, are satisfied. In other words, the determination function 59 determines the timing of main scanning for the subject. Details of processing of the determination function 59 will be described later.

The determination function 59 is an example of a "determiner." The determination function 59 determines the timing of main scanning for the subject on the basis of comparison between data from which a plurality of types of contrast-enhancing substances can be discriminated, generated by the reconstruction function 53 and the determination conditions set for each of the plurality of types of contrast-enhancing substances. The determination function 59 determines the timing of main scanning on the basis of comparison between the calculated contrast effect and the determination conditions.

The display control function 60 causes the display 42 to display a medical image (CT image) generated by the processing circuitry, a GUI image for receiving various operations of an operator such as a doctor or an engineer, and the like. The display control function 60 causes the display 42 to display CT images in which display modes of the plurality of types of contrast agents are different.

The display control function 60 is an example of a "display controller." The display control function 60 causes the display 42 (display device) to display an image in which the display modes of the plurality of types of contrast-enhancing substances are different on the basis of data from which the plurality of types of contrast-enhancing substances can be discriminated, generated by the reconstruction function 53. The display control function 60 causes the display device to display an image in which colors or patterns of the plurality of types of contrast-enhancing substances are different.

With the above configuration, the X-ray CT apparatus 1 scans the subject P in scanning modes such as helical scanning, conventional scanning, and step-and-shoot. Helical scanning is a mode in which the subject P is helically scanned by rotating the rotating frame 17 while moving the top plate 33. Conventional scanning is a mode in which the subject P is scanned in a circular orbit by rotating the rotating frame 17 in a state in which the top plate 33 is stationary. Step-and-shoot is a mode in which the position of the top plate 33 is moved at regular intervals to perform conventional scanning in a plurality of scan areas.

[Processing Flow]

Figure 3:
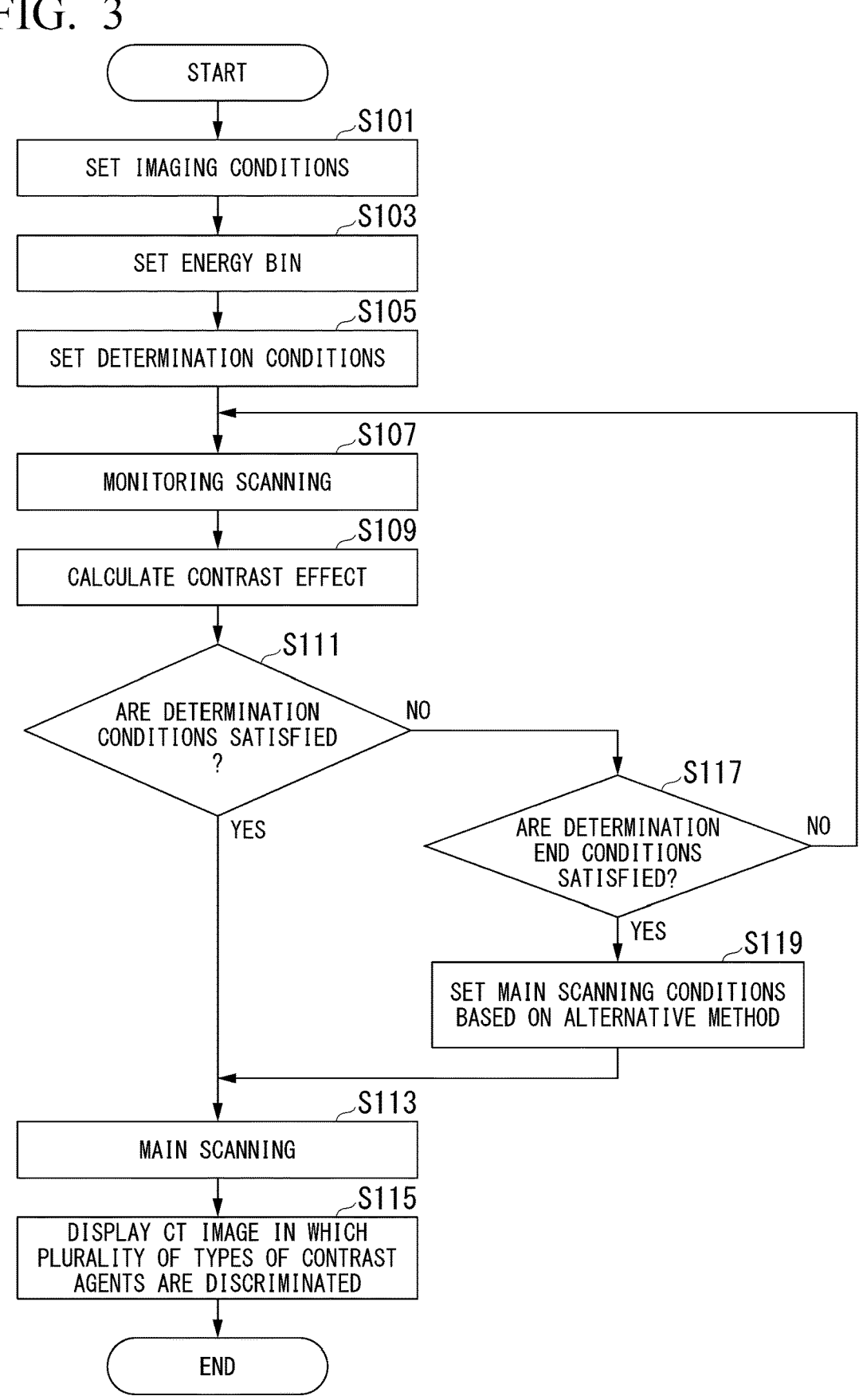
FIG. 3 is a flowchart showing an example of imaging processing of the X-ray CT apparatus 1 according to an embodiment.

Next, an example of imaging processing of the X-ray CT apparatus 1 will be described. FIG. 3 is a flowchart showing an example of imaging processing of the X-ray CT apparatus 1 according to an embodiment. In the following, an example of a case in which imaging is performed using a first contrast agent that is an iodine contrast agent and a second contrast agent that is a gadolinium contrast agent will be described. The first contrast agent and the second contrast agent are sequentially injected into a subject with a time difference.

First, the imaging condition setting function 56 sets imaging conditions on the basis of an input operation received through the input interface 43 (step S101). The imaging condition setting function 56 sets the types of contrast agents used for imaging, a region of interest (arterial phase, venous phase, tissue, etc.) for each contrast agent, the purpose of examination, and the like as imaging conditions.

Subsequently, the system control function 51 sets an energy bin on the basis of the imaging conditions set by the imaging condition setting function 56 (step S103). The system control function 51 outputs setting information of the set energy bin to the control device 18. The system control function 51 may set energy bins on the basis of an input operation received through the input interface 43.

Figure 4:
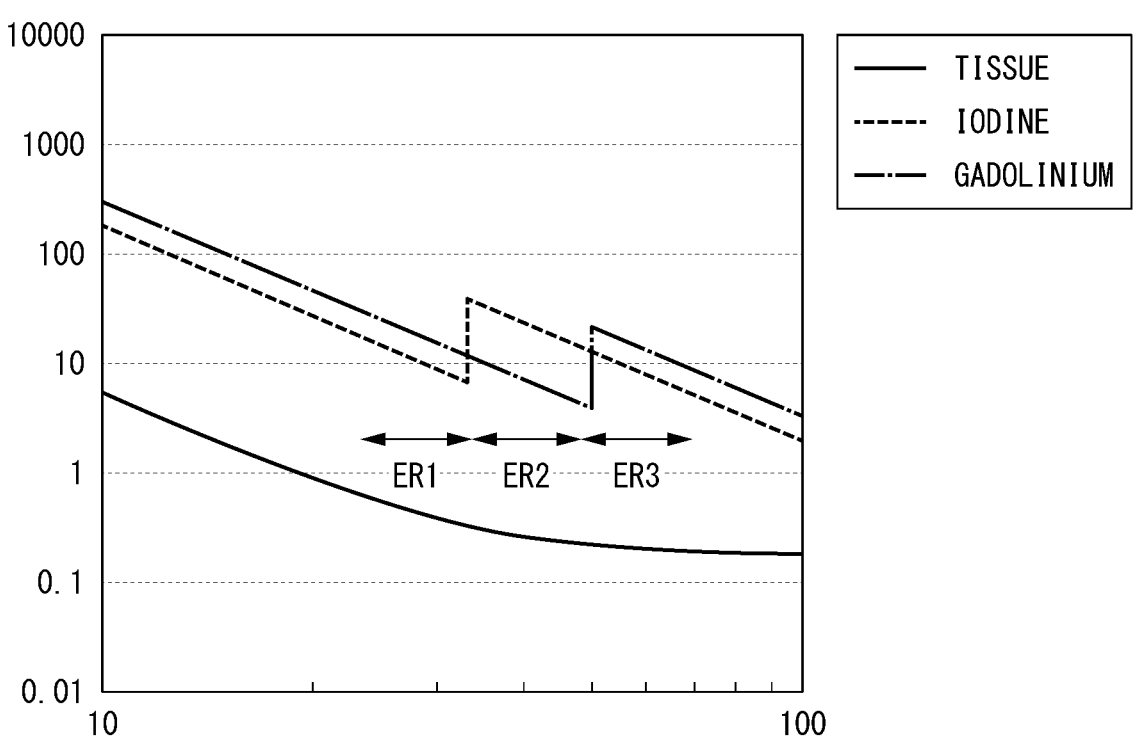
FIG. 4 is a diagram showing a relationship between an X-ray absorption amount and an energy range for each substance according to an embodiment.

FIG. 4 is a diagram showing a relationship between an X-ray absorption amount and an energy range for each substance according to an embodiment. For example, iodine has a point (K-edge) at which the X-ray absorption amount increases at the boundary between an energy range ER1 and an energy range ER2. Gadolinium has a point (K-edge) at which the X-ray absorption amount increases at the boundary between the energy range ER2 and an energy range ER3. In a case where imaging using the first contrast agent that is an iodine contrast agent and the second contrast agent that is a gadolinium contrast agent is performed, an energy bin suitable for discrimination between these two contrast agents is set. An energy bin is appropriately set according to the types of contrast agents used and the purpose of examination.

Subsequently, the determination condition setting function 57 sets determination conditions on the basis of the imaging conditions set by the imaging condition setting function 56 (step S105). The determination condition setting function 57 stores the set determination conditions in the memory 41. The determination condition setting function 57 may set determination conditions on the basis of an input operation received through the input interface 43.

Figures 5, 6:
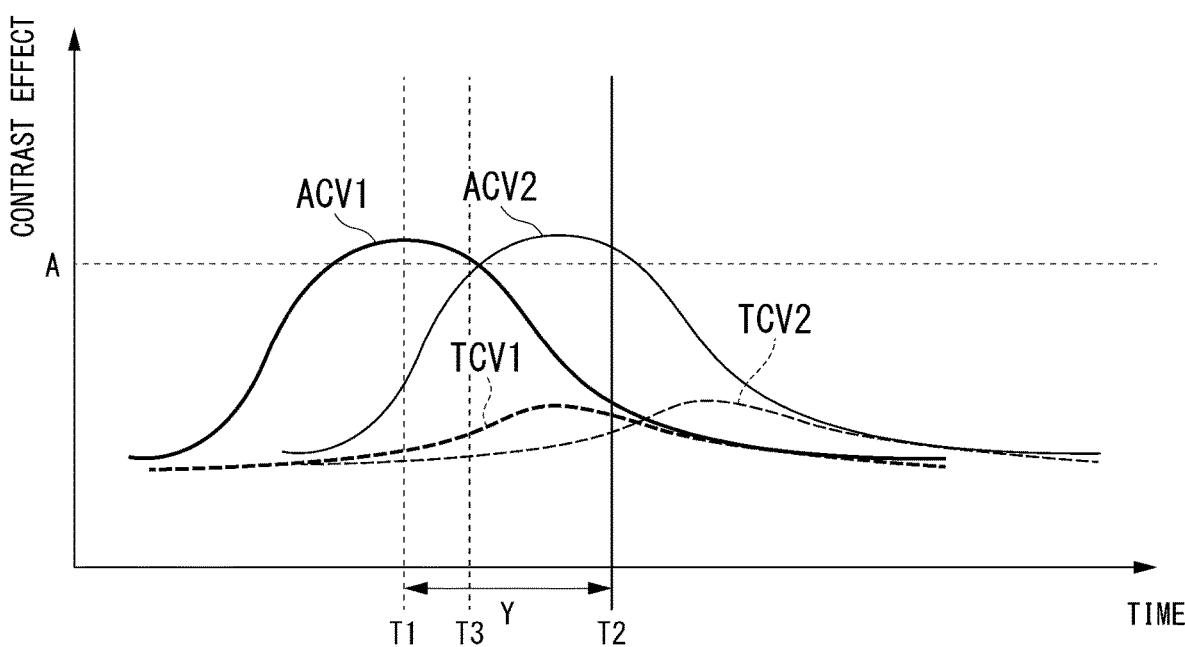
FIG. 5 is a diagram showing an example of determination conditions set for each contrast agent according to an embodiment.
FIG. 6 is a diagram showing determination processing performed by a determination function 59 according to an embodiment.

FIG. 5 is a diagram showing an example of determination conditions set for each contrast agent according to an embodiment. The determination conditions C2 are set by determination conditions set for each contrast agent or a combination of determination conditions set for each contrast agent. Determination conditions are defined on the basis of at least one of C2, an upper limit threshold value of the contrast effect, a lower limit threshold value of the contrast effect, an elapsed time after exceeding a threshold value or a peak value of the contrast effect, an upward trend of the contrast effect, and a downward trend of the contrast effect. In the example shown in FIG. 5, different determination conditions are associated with each of condition numbers 1 to 5 with respect to the first contrast agent. For example, "condition number 1" is associated with a determination condition "A has been exceeded." This "A" (the same applies to "B" and "C") is an index value indicating the contrast effect. For example, this index value is a value based on an X-ray absorption amount. The determination condition setting function 57 sets, for example, a combination of determination conditions for the first contrast agent and determination conditions for the second contrast agent as determination conditions.

Subsequently, the scan control function 55 starts monitoring scanning while the contrast agents are being injected with the subject P placed on the bed (step S107). Here, the first contrast agent and the second contrast agent are sequentially injected into the subject for example.

Subsequently, the contrast effect calculation function 58 calculates the contrast effect (step S109). For example, the reconstruction function 53 calculates the X-ray absorption amount for each of the plurality of types of contrast agents (ground substances) as the contrast effect during monitoring scanning.

Subsequently, the determination function 59 determines whether or not the determination conditions C2 stored in the memory 41 are satisfied (step S111). FIG. 6 is a diagram showing determination processing performed by the determination function 59 according to the embodiment. Here, an example of a case in which a determination condition set for the first contrast agent is "Y seconds have elapsed since a peak was passed (for example, "2 seconds" have elapsed) (condition number 5)," a determination condition set for the second contrast agent is "A has been exceeded," and a combination of these individual determination conditions for the respective contrast agents is used as final determination conditions will be described. Here, it is assumed that a region of interest set for the first contrast agent is a venous phase and a region of interest set for the second contrast agent is an arterial phase. Graph ACV1 shows temporal changes in the contrast effect of the first contrast agent in the arterial phase. Graph TCV1 shows temporal changes in the contrast effect of the first contrast agent in a specific tissue (tumor, etc.). Graph ACV2 shows temporal changes in the contrast effect of the second contrast agent in the arterial phase. Graph TCV2 shows temporal changes in the contrast effect of the second contrast agent in a specific tissue (tumor, etc.).

With respect to the determination condition "Y seconds have elapsed since the peak was passed (for example, "2 seconds" have elapsed)" set for the first contrast agent, graph TCV1 shows a peak at a time T1, and the time at which Y seconds have elapsed from time T1 is T2. Therefore, the individual determination condition set for the first contrast agent is satisfied at the time T2. On the other hand, with respect to the individual determination condition "A has been exceeded" set for the second contrast agent, graph TCV2 exceeds A at a time T3. Therefore, the individual determination condition set for the second contrast agent is satisfied at the time T3. In this case, the determination function 59 determines that determination conditions are satisfied at "time T2" at which the final determination conditions corresponding to a combination of the individual determination condition for the first contrast agent and the individual determination condition for the second contrast agent are satisfied (the two individual determination conditions are satisfied).

In a case where the determination function 59 determines that the determination conditions are satisfied (step S111: YES), the scan control function 55 starts main scanning (step S113). According to this main scanning, for example, imaging can be performed in a state in which, in the subject, the first contrast agent has been injected into the venous phase corresponding to the region of interest, the second contrast agent has been injected into the arterial phase corresponding to the region of interest, and both the first contrast agent and the second contrast agent are reflected in one image.

On the other hand, in a case where the determination function 59 determines that the determination conditions are not satisfied (step S111: NO), the determination function 59 determines whether or not determination end conditions are satisfied (step S117). It is assumed that preset determination conditions will never be satisfied depending on the condition of the subject, and the like. Therefore, as a preliminary measure, the determination function 59 determines whether or not the determination end conditions are satisfied (determines whether or not to continue determination processing for predetermined determination conditions). The determination end conditions are that a predetermined time has elapsed since injection of a contrast agent, that the contrast effect of the contrast agent has decreased below a threshold value, and the like, for example. In a case where the determination function 59 determines that the determination end conditions are not satisfied (step S117: NO), the determination function 59 returns to step S111 and repeats determination for the determination conditions.

On the other hand, in a case where the determination function 59 determines that the determination end conditions are satisfied (step S117: YES), the scan control function 55 sets main scanning conditions on the basis of an alternative method (step S119). For example, as an alternative method, a method of acquiring a curve showing temporal change in detection data for each contrast agent by injecting each contrast agent into the subject in advance (test injection), identifying a contrast time phase on the basis of a peak value of each curve, and determining a timing of main scanning on the basis of a difference between contrast time phases can be used. A contrast time phase refers to an elapsed time from a predetermined reference time such as a time from the start of injection of a contrast agent or a time from the passage of a contrast agent through a predetermined position. Subsequently, the scan control function 55 starts main scanning on the basis of the main scanning conditions set through the alternative method (step S113). According to this main scanning, for example, imaging can be performed in a state in which, in the subject, the first contrast agent has been injected into the venous phase corresponding to the region of interest, the second contrast agent has been injected into the arterial phase corresponding to the region of interest, and both the first contrast agent and the second contrast agent are reflected in one image. In a case where it is not possible to determine the timing of main scanning even by the alternative method, a timing may be determined such that each of the plurality of types of contrast agents is individually imaged.

Figure 7:
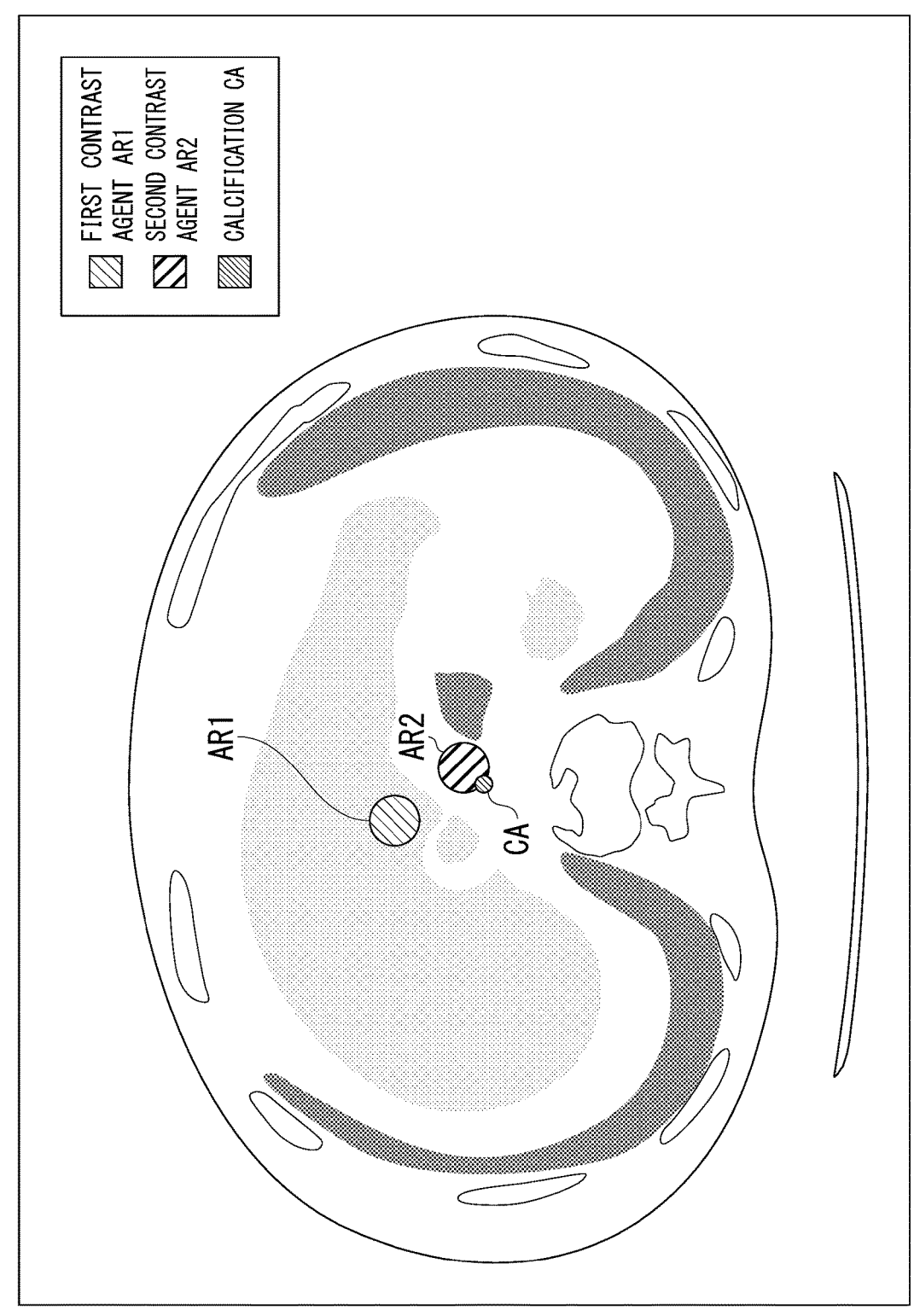
FIG. 7 is a diagram showing an example of a CT image IMG captured through main scanning according to an embodiment.

After main scanning is finished, the display control function 60 causes the display 42 to display a CT image (CT image displaying different display modes of the plurality of types of contrast agents) in which the plurality of types of contrast agents are discriminated, generated by the reconstruction function 53, on the basis of the display conditions C1 stored in the memory 41 (step S115). FIG. 7 is a diagram showing an example of a CT image IMG captured by main scanning according to the embodiment. The CT image IMG is an image captured at the timing when the first contrast agent is positioned at a venous phase position AR1 and the second contrast agent is positioned at an arterial phase position AR2. For reference, the CT image IMG also shows a calcification position CA. With the above, processing of this flowchart ends.

According to the embodiments described above, imaging in a case where a plurality of types of contrast-enhancing substances are used is optimally controlled by including the reconstruction function 53 (reconstructor) that generates data from which the plurality of types of contrast-enhancing substances can be discriminated on the basis of detection results obtained by monitoring scanning performed on a subject into which the plurality of types of contrast-enhancing substances are injected. In particular, it is possible to capture an image in which each of the plurality of types of contrast-enhancing substances injected into the subject is positioned in a predetermined region of interest through one main scanning. This eliminates the need for procedures such as positioning that are required when a plurality of types of contrast-enhancing substances are imaged separately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon counting computed tomography (CT) apparatus comprising:

a memory storing determination condition information in which different determination conditions are associated with each of a plurality of types of contrast-enhancing substances, the determination conditions defining conditions for determining a timing of main scanning at a time of performing imaging using the plurality of types of contrast-enhancing substances and being defined on a basis of at least one of an upper limit threshold value of a contrast effect, a lower limit threshold value of the contrast effect, and an elapsed time from exceeding a threshold value or a peak value of the contrast effect; and processing circuitry configured to:
   generate data from which the plurality of types of contrast-enhancing substances are able to be discriminated on the basis of detection results obtained by monitoring scanning performed on a subject into which the plurality of types of contrast-enhancing substances have been injected;
   calculate the contrast effect of each of the plurality of types of contrast-enhancing substances on the basis of the data from which the plurality of types of contrast-enhancing substances are able to be discriminated;

determine whether or not the calculated contrast effect of each of the plurality of types of contrast-enhancing substances satisfies determination conditions corresponding to a combination of determination conditions set for each of the plurality of types of contrast-enhancing substances injected into the subject; and start main scanning for the subject at a timing when determining that the calculated contrast effect of each of the plurality of types of contrast-enhancing substances satisfies the determination conditions, wherein, when determining that the calculated contrast effect of each of the plurality of types of contrast-enhancing substances does not satisfy the determination conditions, the processing circuitry is configured to:

perform re-monitoring scanning on the subject and re-generating data from which the plurality of types of contrast-enhancing substances are able to be discriminated on the basis of detection results obtained by the re-monitoring scanning;

re-calculate the contrast effect of each of the plurality of types of contrast-enhancing substances on the basis of the re-generated data from which the plurality of types of contrast-enhancing substances are able to be discriminated; and re-determine whether or not the re-calculated contrast effect of each of the plurality of types of contrast-enhancing substances satisfies the determination conditions set for each of the plurality of types of contrast-enhancing substances injected into the subject.

2. The photon counting CT apparatus according to claim 1, wherein the processing circuitry is configured to cause a display device to display an image in which display modes of the plurality of types of contrast-enhancing substances are different on the basis of the generated data from which the plurality of types of contrast-enhancing substances are able to be discriminated.

3. The photon counting CT apparatus according to claim 2, wherein the processing circuitry is configured to cause the display device to display the image in which colors or patterns of the plurality of types of contrast-enhancing substances are different.

4. The photon counting CT apparatus according to claim 1, wherein the plurality of types of contrast-enhancing substances are contrast agents sequentially injected into the subject with a time difference.

5. An imaging method, using a photon counting computed tomography (CT) apparatus comprising a memory storing determination condition information in which different determination conditions are associated with each of a plurality of types of contrast-enhancing substances, the determination conditions defining conditions for determining a timing of main scanning at a time of performing imaging using the plurality of types of contrast-enhancing substances and being defined on the basis of at least one of an upper limit threshold value of a contrast effect, a lower limit threshold value of the contrast effect, and an elapsed time from exceeding a threshold value or a peak value of the contrast effect, the imaging method, comprising:

generating data from which the plurality of types of contrast-enhancing substances are able to be discriminated on the basis of detection results obtained by monitoring scanning performed on a subject into which the plurality of types of contrast-enhancing substances have been injected;

calculating the contrast effect of each of the plurality of types of contrast-enhancing substances on the basis of the data from which the plurality of types of contrast-enhancing substances are able to be discriminated;

determining whether or not the calculated contrast effect of each of the plurality of types of contrast-enhancing substances satisfies determination conditions set for each of the plurality of types of contrast-enhancing substances injected into the subject; and starting main scanning for the subject at a timing when determining that the calculated contrast effect of each of the plurality of types of contrast-enhancing substances satisfies the determination conditions, wherein, when determining that the calculated contrast effect of each of the plurality of types of contrast-enhancing substances does not satisfy the determination conditions, the imaging method further comprises:

performing re-monitoring scanning on the subject and re-generating data from which the plurality of types of contrast-enhancing substances are able to be discriminated on the basis of detection results obtained by the re-monitoring scanning;

re-calculating the contrast effect of each of the plurality of types of contrast-enhancing substances on the basis of the re-generated data from which the plurality of types of contrast-enhancing substances are able to be discriminated; and re-determining whether or not the re-calculated contrast effect of each of the plurality of types of contrast-enhancing substances satisfies the determination conditions set for each of the plurality of types of contrast-enhancing substances injected into the subject.

* * * * *